United States Patent
Fabian et al.

(10) Patent No.: US 6,849,762 B2
(45) Date of Patent: Feb. 1, 2005

(54) PROCESS FOR PREPARING A TRIFLUOROETHOXY-SUBSTITUTED BENZOIC ACID

(75) Inventors: Kai Fabian, Wilhelmsfeld (DE); Steffen Enke, Neckarhausen (DE); Herbert Tilly, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 84 days.

(21) Appl. No.: 10/296,065

(22) PCT Filed: May 23, 2001

(86) PCT No.: PCT/EP01/05923

§ 371 (c)(1),
(2), (4) Date: Nov. 21, 2002

(87) PCT Pub. No.: WO01/90062

PCT Pub. Date: Nov. 29, 2001

(65) Prior Publication Data

US 2003/0176721 A1 Sep. 18, 2003

(30) Foreign Application Priority Data

May 23, 2001 (DE) .......................................... 100 25 700

(51) Int. Cl.$^7$ .............................................. C07C 65/00
(52) U.S. Cl. ........................ 562/474; 562/476; 562/478
(58) Field of Search .................................. 562/474, 476, 562/478

(56) References Cited

FOREIGN PATENT DOCUMENTS

| DE | 3931954 | * | 3/1990 |
| WO | WO 98/47853 | * | 10/1998 |

OTHER PUBLICATIONS

Jay Wrobel et al., "Syntheses of Tolrestat Analogues Containing Additional Substituents in the Ring and Their Evaluation as Aldose Reductase Inhibitors. Identification of Potent, Orally Active 2–Fluoro Derivatives", J. Med. Chem. 1991, 34, pp. 2504–2520.

Search Report for International Application No. PCT/EP01/05923 dated Feb. 5, 2002.

* cited by examiner

Primary Examiner—Rita Desai
Assistant Examiner—Hector M. Reyes
(74) Attorney, Agent, or Firm—Millen White Zelano & Branigan, P.C.

(57) ABSTRACT

The invention relates to a method for the production of trifluoroethoxy-substituted benzoic acids, by reaction of a corresponding halogenated benzoic acid with trifluoroethanol in the solvent tetrahydrofuran, in the presence of a base and a copper salt, followed by an acidic work-up.

18 Claims, No Drawings

PROCESS FOR PREPARING A TRIFLUOROETHOXY-SUBSTITUTED BENZOIC ACID

The invention relates to a process for the preparation of trifluoroethoxy-substituted benzoic acids of the formula I

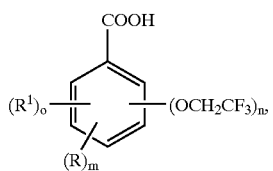

in which
R and $R^1$ are each, independently of one another, A, OA, COOH, COOA, SA, $CF_3$, $OCF_3$, CN, $NO_2$, Hal, $-(CH_2)_p$-Hal, $-O-(CH_2)_p$-Hal, $-S-(CH_2)_p$-Hal, Ar, $-(CH_2)_p-$Ar, OAr, O(CO)Ar, $NH_2$, NHA, $NA_2$, $CONH_2$, CONHA or $CONA_2$,
A is an alkyl radical having from 1 to 4 carbon atoms,
Ar is phenyl or naphthyl, each of which is unsubstituted or monosubstituted, disubstituted or trisubstituted by A, OH, OA, $CF_3$, $OCF_3$, CN or $NO_2$,
Hal is F, Cl, Br or I,
n is 1, 2 or 3,
m and o are each, independently of one another, 0, 1 or 2,
p is 1 or 2,
by reaction of a compound of the formula II

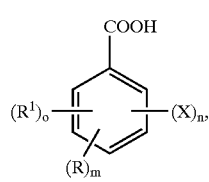

in which
X is Cl, Br or I, and
R, $R^1$, A, Ar, Hal, n, m, o and p are as defined in the formula I, where, for n>1, X may be identical or different, with trifluoroethanol in the solvent tetrahydrofuran, in the presence of a base and a copper salt and subsequent acidic work-up.

Trifluoroethoxy-substituted benzoic acid derivatives of the formula I are useful synthesis building blocks, for example for the preparation of medicaments. In particular, the compound 2,5-bis(2,2,2-trifluoroethoxy)benzoic acid is an important intermediate in the synthesis of the active ingredient flecainide acetate, an antiarrhythmic, disclosed in U.S. Pat. No. 3,900,481.

A known process for the preparation of trifluoroethoxy-substituted benzoic acid derivatives of the formula I is described in Banitt et al, J. Med Chem. 1975, 18, 1130. Hydroxyl-substituted benzoic acids or benzoic acid esters are reacted with 2,2,2-trifluoroethyl trifluoromethanesulfonate in a classical nucleophilic substitution.

GB 2045760 describes a process for the preparation of 2,5-bis(2,2,2-trifluoroethoxy)benzoic acid by firstly reacting hydroquinone or 1,4-dibromobenzene with 2,2,2-trifluoroethyl trifluoromethanesulfonate or trifluoroethanolate to give 1,4-di(trifluoroethoxy)benzene, introducing the acetyl group in the o-position to a trifluoroethoxy substituent by acetylation in the presence of a Lewis acid, and subsequently oxidising the product to the desired benzoic acid.

The processes described hitherto require either raw materials which are expensive and of restricted commercial availability or are based on a multi-step synthesis sequence which is impracticable for large-scale industrial use.

These disadvantages are overcome by the one-step synthesis of WO 98/47853. In WO 98/47853, halogenated benzoic acids or salts thereof are reacted with 2,2,2-trifluoroethanol in the presence of a strong base and a copper-containing material and, if desired, subjected to acidic work-up. This reaction type corresponds to an Ullmann reaction. Furthermore, the use of an aprotic solvent, in particular the solvents N,N-dimethylformamide, N-methylpyrrolidone, N,N-dimethylacetamide, pyridine, collidine, dimethyl sulfoxide, hexamethylphosphoric triamide or mixtures thereof, is regarded as advantageous. However, trifluoroethanol can also itself be used as solvent. Strong bases which are suitable for the process described are sodium, NaH, $NaNH_2$, sodium alkoxides or potassium alkoxides, NaOH, KOH, nitrogen-substituted amidines, guanidines or tetraalkylammonium hydroxides. Sodium hydride is disclosed as a particularly preferred base.

The reaction temperature is, owing to DMF as preferred solvent, preferably 110–115° C.

After acidic hydrolysis, the reaction product precipitates together with the resultant copper salts and by-products and is filtered off. The residue is firstly taken up in 5% KOH, and the solution is filtered through Celite. The alkaline solution which remains is extracted a number of times with, for example, dichloromethane, and the product is subsequently precipitated from the alkaline solution using hydrochloric acid and recrystallised.

However, the system NaH with the solvents listed above, in particular DMF, has a high safety risk for large-scale industrial synthesis since this system can decompose exothermically in an uncontrollable manner (Lit.: Gordon DeWall, C&EN, 1982, September 13, pp. 42–43). Hydrogen is always formed additionally in the hydrolysis of the sodium hydride which remains, in turn entailing a second safety risk. Neither does changing to other bases, for example the use of sodium tert-butoxide or potassium tert-butoxide, in combination with the solvents disclosed in WO 98/47853, in particular DMF, result in reaction controllability which is satisfactory with respect to the safety requirements for large-scale industrial syntheses. The process disclosed in WO 98/47853, as described above, is therefore only suitable for reactions on a laboratory scale.

The invention therefore had the object of developing an improved process for the preparation of trifluoroethoxy-substituted benzoic acid derivatives of the formula I. The improved process should be suitable, in particular, for large-scale industrial synthesis.

The process according to the invention represents a selection invention with respect to the process described in WO 98/47853.

Surprisingly, it has been found that the reaction of the halogenated benzoic acid derivatives of the formula II, as described above, with trifluoroethanol in the presence of a base and a copper salt on use of the solvent THF in the presence of the bases sodium, NaH, $NaNH_2$, Na alkoxide or K alkoxide, NaOH or KOH, in particular in the presence of potassium tert-butoxide, results in a reaction which is very readily controllable from a safety point of view.

The conversion of the starting materials into the trifluoroethoxy-substituted benzoic acid derivatives of the formula I succeeds in good to very good yields at a reaction temperature of about 70° C. which is comparatively low compared with WO 98/47853.

Furthermore, the use of the solvent tetrahydrofuran in the presence of dilute hydrochloric acid simplifies the removal of the resultant copper salts from the reaction. The work-up in accordance with the process according to the invention requires a lower number of working steps compared with WO 98/47853 since the product remains dissolved in THF, while the copper salts and by-products remain predominantly in the aqueous phase. In particular, post-extraction with a halogenated solvent, as described for the process of WO 98/47853, is superfluous.

Due to the lower reaction temperature compared with the preferred system of WO 98/47853, as described above, the formation of by-products is suppressed, giving products with high purity.

The invention therefore relates to a process for the preparation of trifluoroethoxy-substituted benzoic acids of the formula I

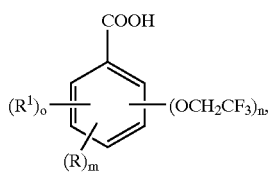

in which

R and $R^1$ are each, independently of one another, A, OA, COOH, COOA, SA, $CF_3$, $OCF_3$, CN, $NO_2$, Hal, $—(CH_2)_p$-Hal, $—O—(CH_2)_p$-Hal, $—S—(CH_2)_p$-Hal, Ar, $—(CH_2)_p$—Ar, OAr, O(CO)Ar, $NH_2$, NHA, $NA_2$, $CONH_2$, CONHA or $CONA_2$, A is an alkyl radical having from 1to 4 carbon atoms, Ar is phenyl or naphthyl, each of which is unsubstituted or monosubstituted, disubstituted or trisubstituted by A, OH, OA, $CF_3$, $OCF_3$, CN or $NO_2$, Hal is F, Cl, Br or I, n is 1, 2 or 3, m and o are each, independently of one another, 0, 1 or 2, p is 1 or 2, by reaction of a compound of the formula II

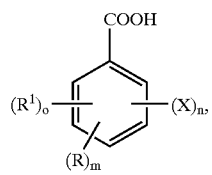

in which

X is Cl, Br or I, and

R, $R^1$, A, Ar, Hal, n, m, o and p are as defined in the formula I, where, for n>1, X may be identical or different, with trifluoroethanol in the solvent tetrahydrofuran, in the presence of a base and a copper salt and subsequent acidic work-up.

The process according to the invention, as described above, is particularly suitable for large-scale industrial syntheses, i.e. preferably for the preparation of products in the range from 1 kg to 500 kg.

In the above formulae, A is alkyl and has from 1 to 4, preferably 1, 2 or 3, carbon atoms. Alkyl is preferably methyl, furthermore ethyl, propyl, isopropyl, butyl, isobutyl, sec-butyl or tert-butyl. A is particularly preferably methyl.

Ar is preferably unsubstituted phenyl or naphthyl, furthermore preferably phenyl which is monosubstituted, disubstituted or trisubstituted by A, OH, OA, $CF_3$, $OCF_3$, CN or $NO_2$. A has one of the preferred meanings indicated above. Ar is particularly preferably unsubstituted phenyl.

$—(CH_2)_p$—Ar, where p=1 or 2, is also arylalkyl and is preferably benzyl, phenylethyl or naphthylmethyl, particularly preferably benzyl.

O(CO)Ar is preferably benzoyl.

Hal is preferably F or Cl.

X is preferably Cl or Br.

R or $R^1$ are each, independently of one another, A, OA, COOH, COOA, SA, $CF_3$, $OCF_3$, CN, $NO_2$, Hal, $—(CH_2)_p$-Hal, $—O—(CH_2)_p$-Hal, $—S—(CH_2)_p$-Hal, Ar $—(CH_2)_p$—Ar, OAr, O(CO)Ar, $NH_2$, NHA, $NA_2$, $CONH_2$, CONHA or $CONA_2$. R and $R^1$, each independently of one another, are particularly preferably A, OA or $NH_2$. R and $R^1$ are very particularly preferably H.

p is preferably 1.

n is preferably 1 or 2, particularly preferably 2.

m is preferably 0 or 1, particularly preferably 0.

o is preferably 0.

The process according to the invention is particularly preferably suitable for the synthesis of 2,5-bis(2,2,2-trifluoroethoxy)benzoic acid.

The halogenated benzoic acid derivatives of the formula II are commercially available or can be prepared by methods known per se, as described, for example, in Houben-Weyl, Methoden der Organ. Chemie [Methods of Organ. Chemistry]. A preferred starting material for the synthesis of 2,5-bis(2,2,2-trifluoroethoxy)benzoic acid is 5-bromo-2-chlorobenzoic acid. Furthermore, the use of a salt of the benzoic acid derivatives of the formula II, for example a sodium benzoate or potassium benzoate of the formula II, is also suitable as starting material in the process according to the invention.

Phase-transfer catalysts from the class of the tris (polyoxaalkyl)amines for Ullmann or Ullmann-analogous reactions are disclosed in the literature (Lit.: G. Soula, J. Org. Chem. 1985, 50, 3717–3721 or Rewcastle et al, J. Med. Chem. 1989, 32, 793–799). Particularly suitable phase-transfer catalysts for the process according to the invention are tris[2-(2-methoxy)-ethoxy]ethylamine (TDA-1) or tris [2-(2-ethoxy)ethoxy]ethylamine (TDA-2), TDA-1being particularly preferred.

The invention relates to a process, as described above, characterised in that the phase-transfer catalyst is a tris (polyoxaalkyl)amine. In a particularly preferred embodiment, the process according to the invention is carried out in the presence of TDA-1.

Suitable bases for the process according to the invention, as described above, are sodium, NaH, $NaNH_2$, Na alkoxide or K alkoxide, NaOH or KOH. Na alkoxides or K alkoxides, for example sodium methoxide or potassium methoxide, sodium ethoxide or potassium ethoxide or sodium tert-butoxide or potassium tert-butoxide, are preferably suitable. Potassium tert-butoxide is particularly preferably used in the process according to the invention. It is possible to omit the use of some or all of the base if a corresponding trifluoroethoxide is employed instead of the trifluoroethanol. For the process according to the invention, sodium trifluoroethoxide or potassium trifluoroethoxide is particularly suitable.

The invention relates to a process, as described above, characterised in that the base is selected from the group consisting of sodium, NaH, $NaNH_2$, Na alkoxide or K alkoxide, NaOH or KOH.

In general, the term copper salts is taken to mean copper (I) salts, for example Cu(I) acetate, Cu(I)Br, Cu(I)Cl, Cu(I)I, Cu(I) oxide, or Cu(I) rhodanide. The copper salts Cu(I)Cl, Cu(I)Br or Cu(I)I are particularly suitable in accordance with the invention, the use of Cu(I)Br being particularly preferred.

The invention likewise relates to a process, as described above, characterised in that the copper salt used is copper(I) iodide or copper(I) bromide.

The reaction according to the invention, as described above, is preferably carried out at temperatures between 10 and 80°, particularly preferably at temperatures between 50 and 70° C. The reaction is very particularly preferably carried out at the boiling point of tetrahydrofuran.

The temperature programme in the process according to the invention is selected in such a way that the starting materials are firstly mixed at temperatures below 35° C., preferably between 10° and 30° C., particularly preferably at 20° C., and the temperature is then increased to the actual reaction temperature between 50° and 80°, in particular to the boiling point of tetrahydrofuran.

The invention also relates to a process, as described, characterised in that the reaction is carried out at temperatures between 10° and 80° C. The invention relates to a process, as described above, in which the starting materials are mixed at a temperature below 35° C., and the temperature of the reaction mixture is increased to a reaction temperature between 50° and 80° C.

The term starting materials with respect to the description of the temperature programme covers all components of the reaction. The term starting materials (in connection with the temperature programme) includes THF, the base, the phase-transfer catalyst, trifluoroethanol, the copper salt and a halogenated benzoic acid of the formula II.

The invention also relates to a process, as described, characterised in that the reaction mixture is subjected to acidic work-up. The acidic hydrolysis is preferably carried out with an acid selected from a group of acids including organic acids, preferably formic acid, acetic acid or propionic acid, or also inorganic acids, preferably sulfuric acid, nitric acid, hydrohalic acids, such as hydrochloric acid or hydrobromic acid, or phosphoric acids, such as orthophosphoric acid. Hydrochloric acid is particularly preferably employed.

Suitable molar ratios of selected components to one another for the process according to the invention is described below.

At least 1 mol of 2,2,2-trifluoroethanol is used per halogen atom of a compound of the formula II, with an excess of trifluoroethanol preferably being used. 3 mol of 2,2,2-trifluoroethanol are particularly preferably employed per halogen atom of a compound of the formula II.

At least 1 mol of 2,2,2-trifluoroethanol is used per mole of base.

The molar ratio of copper salt to a compound of the formula II can be from 0.01:1 to 2:1. A molar ratio of 1:1 is particularly preferred.

The molar ratio of phase-transfer catalyst to a compound of the formula II can be from 0.01:1 to 1:1. A molar ratio of from 0.1:1 to 0.5:1 is preferred, a molar ratio of 0.2:1 is very particularly preferred.

The invention furthermore relates to a process for the preparation of trifluoroethoxy-substituted benzoic acid derivatives of the formula I, characterised in that the base and/or, where used, the phase-transfer catalyst is initially introduced in THF, the phase-transfer catalyst, where used, or the base, if they were not introduced together, is subsequently added, 2,2,2-trifluoroethanol is added dropwise, and the copper salt and the corresponding halogenated benzoic acid of the formula II are added to this reaction mixture successively or at the same time in any desired sequence. After a reaction time of from a few minutes to several hours, the reaction mixture is cooled, and the acid, as described above, is added. The reaction mixture is worked up by methods which are known to the person skilled in the art or as explained in the following examples.

Even without further comments, it is assumed that a person skilled in the art will be able to utilise the above description in the broadest scope. The preferred embodiments should therefore merely be regarded as descriptive disclosure which is absolutely not limiting in any way.

In the following examples and also in the comments above, the temperature is given in ° C. The pH corresponds to the decimal logarithm of the $H^+$ ion concentration.

The purity of the product is determined by an HPLC measurement.

EXAMPLE 1

300 ml of THF are initially introduced at room temperature, and 84.7 g of potassium tert-butoxide are added with stirring 76.0 g of 2,2,2-trifluoroethanol are added dropwise to this reaction mixture, with the temperature being kept below 35° C. When the addition is complete, stirring is continued, and 29.6 g of 5-bromo-2-chlorobenzoic acid are subsequently introduced. After the subsequent addition of 27.3 g of copper(I) bromide, the reaction mixture is heated to reflux.

After 43 hours, the reaction mixture is cooled to 5° C. and allowed to run into dilute hydrochloric acid at 5° C. The organic phase is separated from the aqueous phase, and the solvent is distilled off, during which the product precipitates. 100 ml of water are added to the residue and then filtered. For purification, the crude product is taken up in MTB ether (methyl tert-butyl ether). Undissolved components are separated off by filtration through neutral aluminium oxide, and the solvent is subsequently removed. Recrystallisation from an ethanol/water mixture gives 2,5-bis(2,2,2-trifluoroethoxy)benzoic acid in a yield of 45%.

Melting point: 120–122° C., purity>98% (HPLC).

EXAMPLE 2

Analogously to Example 1, 1500 ml of THF are initially introduced, and 40.4 g of catalysts tris[2-(2-methoxy)ethoxy]ethylamine and subsequently 423.6 g of potassium tert-butoxide are introduced with stirring. After addition of 380.1 g of 2,2,2-trifluoroethanol, 148.2 g of 5-bromo-2-chlorobenzoic acid and 98.8 g of copper(I) bromide, the mixture is worked up as described under Example 1.

Recrystallisation from an ethanol/water mixture gives 2,5-bis(2,2,2-trifluoroethoxy)benzoic acid in a yield of 68%.

Purity>98% (HPLC).

What is claimed is:

1. A process for preparing a trifluoroethoxy-substituted benzoic acid of formula I

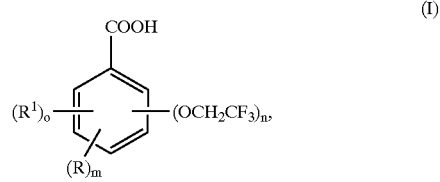

wherein:
R and $R^1$ are each, independently of one another, A, OA, COOH, COOA, SA, $CF_3$, $OCF_3$, CN, $NO_2$, Hal, —$(CH_2)_p$-Hal, —O—$(CH_2)_p$-Hal, —S—$(CH_2)_p$-Hal, Ar, —$(CH_2)_p$—Ar, OAr, O(CO)Ar, $NH_2$, NHA, $NA_2$, $CONH_2$, CONHA or $CONA_2$, A is an alkyl radical having from 1–4 carbon atoms, Ar is phenyl or naphthyl, each of which is unsubstituted or monosubstituted, disubstituted or trisubstituted by A, OH, OA, $CF_3$, $OCF_3$, CN or $NO_2$, Hal is F, Cl, Br or I, n is 1, 2, or 3, m and o are each, independently of one another, 0, 1 or 2, p is 1 or 2;

comprising introducing potassium tertiary butoxide and tris(polyoxaalkyl)amine in tetrahydrofuran, wherein potassium tertiary butoxide, if they are not introduced together, is subsequently added;
adding dropwise 2,2,2-trifluoroethanol; and
adding copper(I) bromide and a compound of formula II

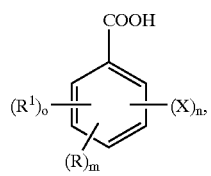

wherein

X is Cl, Br or I, and for n>1, X may be identical or different; to this reaction mixture successively or at the same time in any desired sequence to react the compound of the formula II, and subsequent acidic work-up.

2. A process according to claim 1, wherein the reaction is carried out at a temperature of 10°–80° C.

3. A process according to claim 1, wherein 2,5-bis(2,2,2-trifluoroethoxy)benzoic acid is prepared.

4. A process according to claim 2, wherein 2,5-bis(2,2,2-trifluoroethoxy)benzoic acid is prepared.

5. A process according to claim 1, wherein A is methyl.

6. A process according to claim 1, wherein Ar is unsubstituted phenyl.

7. A process according to claim 1, wherein —$(CH_2)_p$—Ar is benzyl.

8. A process according to claim 1, wherein O(CO)Ar is benzoyl.

9. A process according to claim 1, wherein Hal is F or Cl.

10. A process according to claim 1, wherein X is Cl or Br.

11. A process according to claim 1, wherein R and $R^1$ are H.

12. A process according to claim 1, wherein p is 1.

13. A process according to claim 1, wherein n is 2.

14. A process according to claim 1, wherein m and o are 0.

15. A process according to claim 1, wherein tris(polyoxaalkyl)amine is tris[2-(2-methoxy)-ethoxy]ethylamine or tris[2-(2-ethoxy)ethoxy]ethylamine.

16. A process according to claim 1, wherein tris(polyoxaalkyl)amine is tris[2-(2-methoxy)-ethoxy]ethylamine.

17. A process according to claim 1, wherein the acidic work-up is carried out with hydrochloric acid.

18. A process for preparing trifluoroethoxy-substituted benzoic acid of formula I

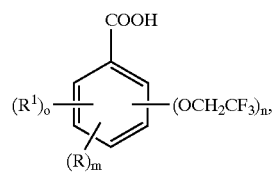

wherein

R and $R^1$ are each, independently of one another, A, OA, COOH, COOA, SA, $CF_3$, $OCF_3$, CN, $NO_2$, Hal, —$(CH_2)_p$-Hal, —O—$(CH_2)_p$-Hal, —S—$(CH_2)_p$-Hal, Ar, —$(CH_2)_p$—Ar, OAr, O(CO)Ar, $NH_2$, NHA, $NA_2$, $CONH_2$, CONHA or $CONA_2$, A is an alkyl radical having from 1–4 carbon atoms, Ar is phenyl or naphthyl, each of which is unsubstituted or monosubstituted, disubstituted or trisubstituted by A, OH, OA, $CF_3$, $OCF_3$, CN or $NO_2$, Hal is F, Cl, Br or I, n is 1, 2, or 3, m and o are each, independently of one another, 0, 1 or 2, p is 1 or 2;

comprising reacting a compound of formula II

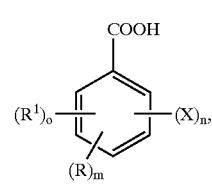

wherein

X is Cl, Br or I, and for n>1, X may be identical or different; with trifluoroethanol in the presence of a tris(polyoxaalkyl)amine.

* * * * *

UNITED STATES PATENT AND TRADEMARK OFFICE
CERTIFICATE OF CORRECTION

PATENT NO. : 6,849,762 B2
DATED : February 1, 2005
INVENTOR(S) : Kai Fabian et al.

It is certified that error appears in the above-identified patent and that said Letters Patent is hereby corrected as shown below:

Title page,
Item [30], Foreign Application Priority Data, "May 23, 2001" should read
-- May 26, 2000 --.

Column 6,
Lines 45-51, Formula (I) should read as follows:

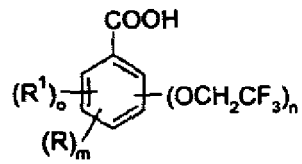

Column 7,
Lines 7-14, Formula (II) should read as follows:

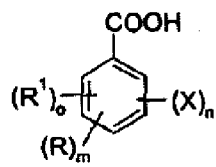

Column 8,
Lines 3-11, Formula (I) should read as follows:

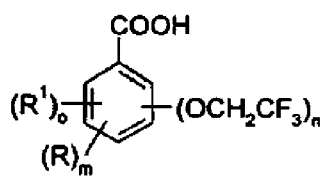

UNITED STATES PATENT AND TRADEMARK OFFICE
CERTIFICATE OF CORRECTION

PATENT NO. : 6,849,762 B2
DATED : February 1, 2005
INVENTOR(S) : Kai Fabian et al.

It is certified that error appears in the above-identified patent and that said Letters Patent is hereby corrected as shown below:

Column 8 (cont'd),
Lines 32-40, Formula (II) should read as follows:

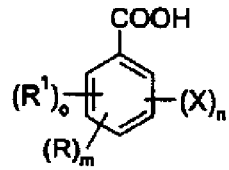

Signed and Sealed this

Seventeenth Day of May, 2005

JON W. DUDAS
*Director of the United States Patent and Trademark Office*